(12) United States Patent
Jaatinen

(10) Patent No.: US 9,938,965 B2
(45) Date of Patent: Apr. 10, 2018

(54) BATTERYLESS ACTIVITY MONITOR

(71) Applicant: Polar Electro Oy, Kempele (FI)

(72) Inventor: Jukka Jaatinen, Kempele (FI)

(73) Assignee: Polar Electro Oy, Kempele (FI)

( * ) Notice: Subject to any disclaimer, the term of this patent is extended or adjusted under 35 U.S.C. 154(b) by 382 days.

(21) Appl. No.: 14/777,976

(22) PCT Filed: Mar. 22, 2013

(86) PCT No.: PCT/FI2013/050324
§ 371 (c)(1),
(2) Date: Sep. 17, 2015

(87) PCT Pub. No.: WO2014/147286
PCT Pub. Date: Sep. 25, 2014

(65) Prior Publication Data
US 2016/0069332 A1    Mar. 10, 2016

(51) Int. Cl.
*H01L 41/113* (2006.01)
*H01L 41/22* (2013.01)
(Continued)

(52) U.S. Cl.
CPC .............. *F03G 7/08* (2013.01); *A61B 5/1118* (2013.01); *G04C 10/04* (2013.01); *G04G 21/02* (2013.01);
(Continued)

(58) Field of Classification Search
USPC .......................... 310/339; 29/25.35; 290/1 R
See application file for complete search history.

(56) References Cited

U.S. PATENT DOCUMENTS 7,944,123 B2 * 5/2011 Gualtieri ................ H02N 2/185
290/43
8,843,241 B2 * 9/2014 Saberi ................. F16K 37/0091
251/129.04
(Continued)

FOREIGN PATENT DOCUMENTS

EP    0 952 500 A1    10/1999
EP    2 260 910 A1    12/2010
WO    96/40522       12/1996

OTHER PUBLICATIONS

International Search Report, Application No. PCT/FI2013/050324, 2 pages, Dec. 2, 2013.

Primary Examiner — Thomas Dougherty
(74) Attorney, Agent, or Firm — Hoffmann & Baron, LLP

(57) ABSTRACT

An apparatus includes at least one base layer arranged as a substrate for printed electronics; an energy harvester printed on the at least one base layer and arranged to transform kinetic energy into electric energy; an energy storage printed on the at least one base layer, coupled to the energy harvester, and arranged to store the electric energy; a display element printed on the at least one base layer, coupled to the energy storage, and arranged to provide a display view to a user of the apparatus; and a control circuitry configured to determine the amount of the electric energy stored in the energy storage and to control the display element to update the display view according to the amount of the electric energy. A method and a computer program product for controlling manufacturing of the apparatus are also disclosed.

14 Claims, 3 Drawing Sheets

(51) Int. Cl.
- *F03G 7/08* (2006.01)
- *G04C 10/04* (2006.01)
- *H01L 41/04* (2006.01)
- *H02N 2/18* (2006.01)
- *G04G 21/02* (2010.01)
- *A61B 5/11* (2006.01)
- *H05K 1/16* (2006.01)

(52) U.S. Cl.
CPC .......... *H01L 41/042* (2013.01); *H01L 41/113* (2013.01); *H02N 2/181* (2013.01); *H02N 2/186* (2013.01); *A61B 2560/0214* (2013.01); *H05K 1/16* (2013.01)

(56) References Cited

U.S. PATENT DOCUMENTS

| | | | | |
|---|---|---|---|---|
| 2013/0082657 A1* | 4/2013 | Rich | .................. | H01L 41/1136 320/114 |
| 2013/0257219 A1* | 10/2013 | Monfray | .................. | H02N 2/18 310/306 |
| 2014/0077662 A1* | 3/2014 | Lueke | ................ | H01L 41/1136 310/339 |

* cited by examiner

BATTERYLESS ACTIVITY MONITOR

CROSS-REFERENCE TO RELATED APPLICATION

This application is a National Stage application of International Application No. PCT/FI2013/050324, filed Mar. 22, 2013, which is incorporated by reference herein in its entirety.

BACKGROUND

Field

The invention relates to the field of activity monitors and, particularly, to an activity monitor without a battery as an energy source.

Description of the Related Art

An activity monitor configured to monitor a user's activity may be based on motion sensing such that an accelerometer or another motion sensor measures the user's motion. The motion sensor may transform mechanical energy into electric signals, and the electric signals may be measured in order to determine an activity level. An example of such an activity monitor is a wrist watch type of activity monitor comprising a battery, a motion sensor, and a liquid crystal display.

SUMMARY

The invention is defined by the independent claims.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
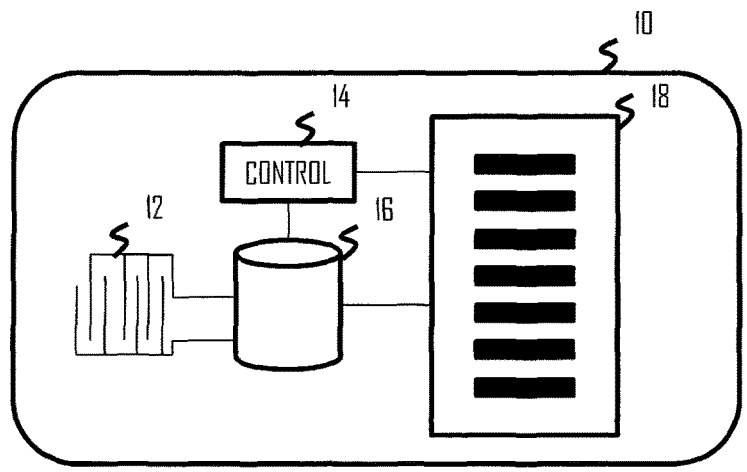
FIGS. 1 and 2 illustrate a structure of an apparatus according to some embodiments of the invention.

FIG. 1 illustrates an embodiment of a structure of an apparatus according to an embodiment of the invention. The apparatus comprises at least one base layer 10 arranged as a substrate for printed electronics. The apparatus further comprises an energy harvester 12 printed on the at least one base layer 10 and arranged to transform kinetic energy focused to the base layer 10 into electric energy. The apparatus further comprises an energy storage 16 printed on the at least one base layer 10. The energy storage 16 is electrically coupled to the energy harvester 12 and arranged to store the electric energy harvested by the energy harvester 12. The apparatus further comprises a display element 18 printed on the at least one base layer 10. The display element 18 is coupled to the energy storage 16 and arranged to provide a display view to a user of the apparatus. The display element 18 may acquire energy it needs for managing the display view from the energy storage 16. The apparatus further comprises a control circuitry 14 coupled to the energy storage 16 and the display element 18. The control circuitry is configured to determine that a sufficient amount of energy is stored in the energy storage 16 and, as a consequence, control the display element 18 to update the display view.

In an embodiment, the electric energy harvested by the energy harvester 12 is thus used as a power supply and as a measurement signal measuring the motion of the apparatus. This dual use improves power-efficiency. The apparatus may be provided without an additional power supply such as a battery.

As mentioned above, the base layer 10 to which the other components 12 to 18 are disposed is made of a material to which printed electronics may be applied. The material may thus be suitable for serving as the substrate for the printed electronics. The material may be flexible material or rigid material. In an embodiment, the material is polycarbonate foil. In another embodiment, the material is dialuminium trioxide ($Al_2O_3$). In yet another embodiment, the material is (poly)ethylene naphthalate (PET). In yet another embodiment, the material is (poly)imide foil (P1). In general, the material may be plastic material but textile or paper material may be equally envisaged as the substrate material.

The components 12 to 18 may be printed on the base layer 10 according to state of the art roll-to-roll manufacturing methods or electronics printing techniques, e.g. inkjet printing techniques.

The energy harvester 12 may be based on piezoelectricity and it may comprise a printed piezo element. The piezo element may be printed by printing two electrode layers and by printing piezoelectric material between the electrodes. The electrodes may comprise silver or a silver composition or bariumtitaniumtrioxide ($BaTiO_3$), for example. The piezoelectric material may be dialuminiumtrioxide ($Al_2O_3$) or polycarbonate foil, for example. The electrode layers may be separated from each other by the piezoelectric material along the plane of the base layer, as shown in FIG. 1, and/or they may be provided as layers on top of each other on the base layer 10.

The energy storage 16 may be designed as a capacitor, for example. The capacitor may be printed by printing electrodes and an insulator between the electrodes. The electrodes may be made of materials described above in connection with the electrodes of the energy harvester 12. The insulator may be made of titanium dioxide ($TiO_2$), for example.

The display element 18 may be a multi-stable display element, i.e. it may require energy only for the update of the display view. In an embodiment, the display element 18 is based on electronic ink display techniques, e.g. it may be an electrophoretic display. An advantage of using the multi-stable display is that it does not consume the electric energy from the energy storage 16 during times when the energy harvester 12 is idle. The display element 18 may be preconfigured to display a determined sequence of display views when it receives energy from the energy storage 16. As shown in FIG. 1, the display element 18 may be configured to display a determined number of visual elements such as bars and increment the number of displayed elements by one when it receives a new burst of energy from the energy storage 16. In this manner, the number of displayed elements is proportional to the amount of energy harvested by the energy harvester 12 and the amount of motion detected by the energy harvester 12.

In an embodiment, a bar represents a predetermined energy expenditure of a user. A bar may indicate, for example, an increase of 100 kilocalories in the accumulated energy expenditure.

In an embodiment, a bar represents a predetermined amount of physical accumulated activity of the user. A bar may indicate, for example, an increase of 10 minutes in accumulated activity.

In an embodiment, a bar represents a fulfillment of a recommended or classified level of accumulated activity or energy expenditure. One bar may indicate "health activity zone, two bars may indicate "fitness activity zone", and a three bars may indicate "sport activity zone".

The control circuitry 14 may comprise a comparator circuitry or a threshold detector circuitry configured to monitor the amount of energy in the energy storage 16 and, when the sufficient amount of electric energy is stored in the energy storage 16 connect the energy storage 16 to the display element 18 in order to discharge the electric energy from the energy storage 16 to the display element 18 to update the display view. The control circuitry 14 may be configured to compare the amount of stored energy with a threshold and connect the energy storage 16 to the display element 18 when the amount of stored energy exceeds the threshold.

In an embodiment, a threshold corresponds to a predetermined energy expenditure of the user. For example, a certain voltage value stored by a capacitor corresponds to a certain amount of energy consumed by the user. In the case of memsistor, a certain amount of current passed a memristor may correspond to a certain amount of energy consumed by the user.

In an embodiment, a threshold corresponds to an accumulated physical activity accomplished by the user. The physical activity may be proportional to time the user has reached a predetermined activity level.

In an embodiment, a threshold corresponds to an arbitrary activity measure, where the amount of electric energy corresponds to accumulated human motion.

Figure 2:
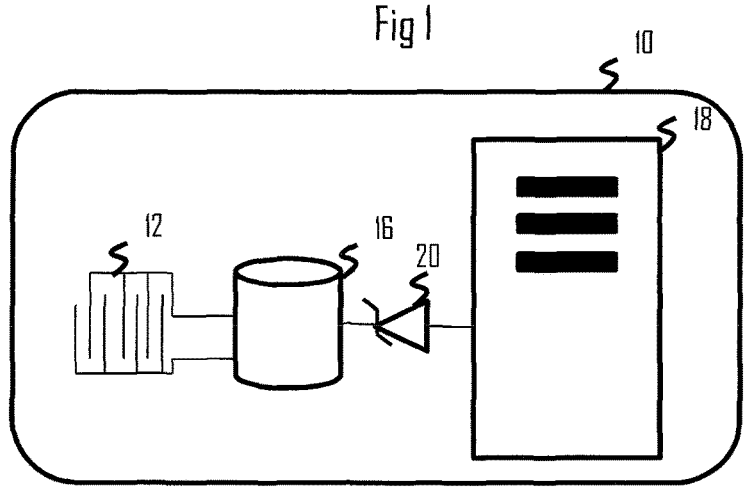

In an embodiment, the control circuitry comprises a zener diode 20 or an avalanche diode disposed between the energy storage 16 and the display element (FIG. 2). As known in the art, the Zener diode 20 may pass electric energy in a reverse direction when its breakdown voltage is exceeded. The avalanche diode exhibits a similar behavior. In some embodiments, the control circuitry 14 may comprise additional components to tune the zener diode 20 or avalanche diode and to ensure that an appropriate amount of energy will be discharged to the display element 18 to update the display view.

In another embodiment, the control circuitry 14 comprises a memristor circuitry. In an embodiment, the control circuitry 14 may be integrated with the energy storage by utilizing memristors. The memristor circuitry may be designed to implement various logic operations which makes suitable for use in the apparatus according to the present invention. As known in the art, a memristor circuitry may be configured to operate as a switch which changes its state after a sufficient amount of energy has been input to the memristor circuitry. In the context of the present invention, the memristor operating as the switch may be configured to be in an open state until the energy harvester 12 has input a determined amount of electric energy into the memristor. After input of the determined amount of electric energy, the memristor may switch its state into a closed state in which it connects to the display element 18 and applies the energy needed for changing the display view to the display element 18. Thereafter, the memristor reverts to the open state until the determined amount of energy is once again input to the memristor.

Figure 3:
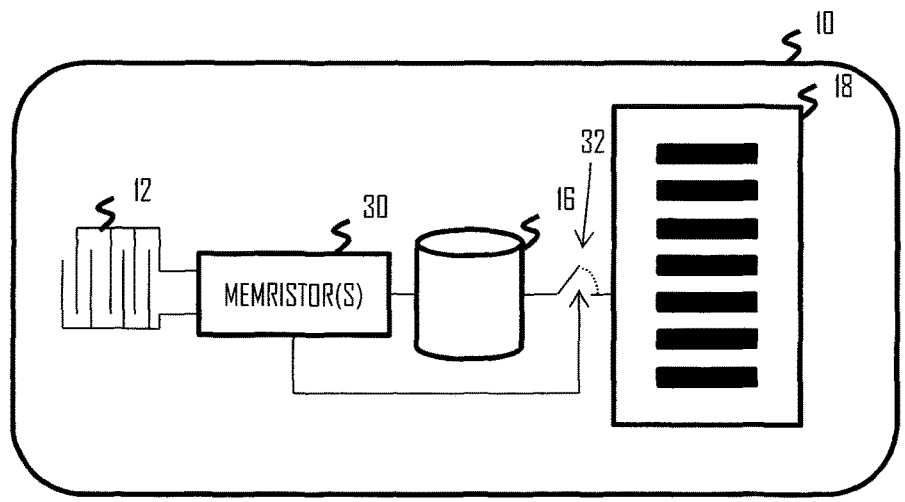
FIGS. 3 and 4 illustrate further embodiments of the structure of the apparatus.
Figure 4:
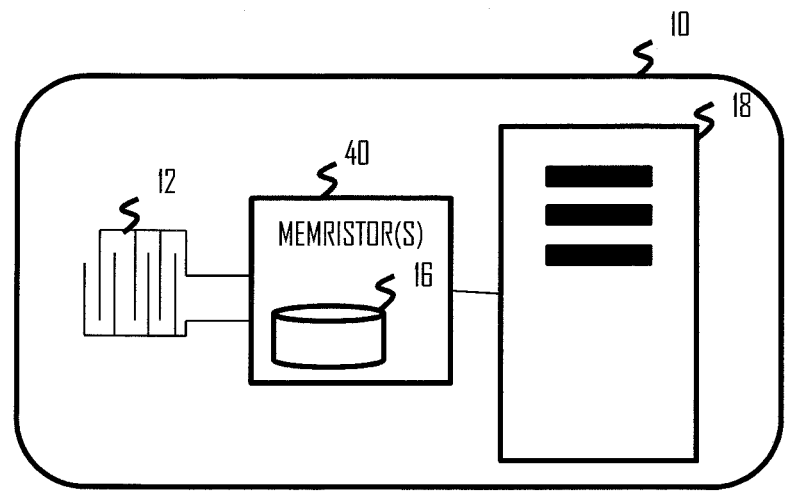

FIGS. 3 and 4 illustrate some embodiments utilizing the memristor(s) as the control circuitry 14. Referring to FIG. 3, the memristor circuitry 30 may be disposed between the energy harvester 12 and the energy storage 16. Additionally, a switch 32 may be disposed between the energy storage 16 and the display element 18 and a control line may be arranged between the switch 32 and the memristor circuitry 30 such that the memristor circuitry 30 may control the switch 32. In an initial state, the switch 32 may be open and disconnect the energy storage 16 from the display element 18. As described above, the memristor circuitry 30 may measure the amount of electric energy received from the energy harvester and output the energy to the energy storage. When a determined amount of energy has been received from the energy harvester 12 and/or input to the energy storage 16, the memristor circuitry may 30 be arranged to output a control signal to the switch 32 and close the switch 32, thus connecting the energy storage 16 to the display element 18 and supplying the display element 18 with electric power from the energy storage. Shortly thereafter, the memristor circuitry 30 may open the switch 32, or the switch 32 may be configured to open autonomously, to enable further accumulation of the energy in the energy storage. In this manner, the memristor circuitry 30 may close the switch 32 again when the sufficient amount of further energy has been accumulated.

FIG. 4 illustrates the embodiment where the memristor circuitry 40 is integrated with the energy storage 16. Referring to FIG. 4, the memristor circuitry 40 may be disposed between the energy harvester 12 and the energy storage 18, and the memristor circuitry 40 may comprise the energy storage, e.g. one or more capacitors. The memristor circuitry may operate as the switch such that it may charge the energy storage with electric energy from the energy harvester 12 until a determined amount of energy has flown through the memristor(s). Thereafter, the memristor(s) may change a state and connect the energy storage 16 to the display element 18 in order to discharge the energy storage 16 to the display element 18 and update the display view. Shortly thereafter, the memristor circuitry 40 may open the connection to the display element in order to enable further accumulation of the energy in the energy storage 16. In this manner, the memristor circuitry 30 may connect the energy storage 16 to the display element again when the sufficient amount of further energy has been accumulated.

In an embodiment, a protective layer may be printed on top of the printed components 12 to 18 to protect them.

As described above, the apparatus may be used as a motion sensor. In an embodiment, the apparatus is an activity sensor configured to measure physical activity of a user. The control circuitry 14 may be configured to control the display element 18 to output an indicator indicating the measured accumulated motion to a user of the apparatus. In FIGS. 1 and 2 the indicator is a combination of bars (other visual elements may be used), wherein the number of displayed bars is proportional to the measured accumulated motion.

Figure 5:
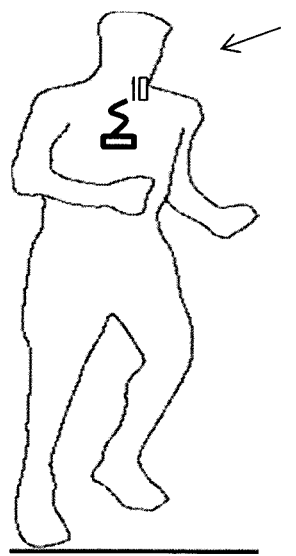
FIGS. 5 and 6 illustrate applications of the apparatus according to some embodiments of the invention.
Figure 6:

FIGS. 5 and 6 illustrate some embodiments of the motion sensor. As the apparatus is realized by printing material on the base layer, the manufacturing and material costs of the apparatus are very low. In an embodiment, the apparatus be disposable. Disposable may mean that the apparatus may be disposed after a single use, e.g. after a maximum amount of motion has been accumulated. The maximum amount may be determined by the capabilities of the display element 18, e.g. when the sequence of display views has reached the final display view, the maximum amount has been accumulated. FIG. 1 may illustrate the maximum amount of displayed indicators, while FIG. 2 illustrates a situation where the final stage has not yet been reached.

In an embodiment, the apparatus comprises an attachment element designed to attach the apparatus to a location where the motion measurements are meant to be carried out, e.g. the user's 11 clothing (see FIG. 5). The attachment element may be based on adhesive attachment or mechanic attachment such as Velcro®. Accordingly, the apparatus may be considered as a sticker configured to function as the activity monitor.

In an embodiment, the disposable apparatus is attachable to the user's 11 body, such as the skin. The user's 11 skin may function as the base layer 10 and the apparatus may be considered as a type of a decal. Alternatively, a separate base layer 10 comprising the components 12 to 18 may be attached to the skin by adhesive coupling. In other embodiments, the apparatus may be used several times even though the maximum amount of accumulated motion has already been measured. The apparatus may comprise a reset circuitry configured to reset the display when the display has reached its final state in the sequence of display views. The reset circuitry may be embedded in the display element. The reset circuitry may autonomously reset the display view, or the reset circuitry may comprise an input mechanism to receive reset instructions from the user 11 via a button, for example.

In an embodiment, the apparatus comprises an attachment structure, such as a band or strap, for attaching the apparatus to the user's body, such as arm, wrist, chest, leg or ankle.

In an embodiment, the threshold with which the amount of stored electric energy is to be compared is chosen according to the motion characteristics of the attachment position on the user. Thus, the threshold is may be different between the cases where the apparatus is attached to the user's chest or the apparatus is attached to the user's wrist, for example.

Figure 7:
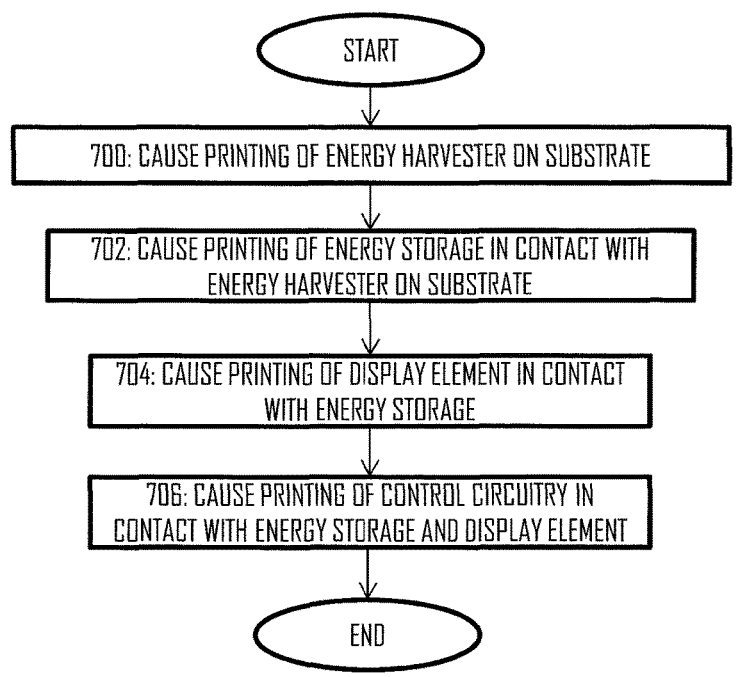
FIG. 7 illustrates a method for manufacturing the apparatus according to an embodiment of the invention.

According to another aspect of the invention, let us describe a method for manufacturing the apparatus according to an embodiment of the invention. The manufacturing method may be realized by a system comprising a printing apparatus configured to print electronics on the substrate and/or a control apparatus configured to control the printing apparatus to print the apparatus according to an embodiment of the invention. FIG. 7 illustrates a flow diagram of the manufacturing method according to an embodiment of the invention. Referring to FIG. 7, the method comprises causing printing of an energy harvester 12 on at least one base layer 10 serving as a substrate for printed electronics, wherein the energy harvester 12 is arranged to transform kinetic energy into electric energy (block 700). The method further comprises causing printing of an energy storage 16 on the at least one base layer 10 and coupling of the energy storage 16 to the energy harvester 12 such that the energy storage 16 stores the electric energy harvested by the energy harvester 12 (block 702). The coupling may be carried out by causing printing of an electric connector between the energy harvester 12 and the energy storage. The method further comprises causing printing of a display element 18 on the at least one base layer 10 and coupling of the display element 18 to the energy storage 12 (block 704), wherein the display element is arranged to provide a display view to a user of the apparatus. The coupling may be carried out by causing printing of an electric connector between the energy storage 16 and the display element 18. The method further comprises causing printing of a control circuitry 14 on the at least one base layer 10 (block 706), wherein the control circuitry 14 is printed such that it is capable of determining that a sufficient amount of energy is stored in the energy storage 16 by the energy harvester 12 and, as a consequence, control the display element 18 to update the display view.

In the above-described embodiment where the energy storage 16 and the control circuitry are integrated together, blocks 702 and 706 may be combined. In general, it should be appreciated that the order of steps 700 to 706 may depend on the design of the apparatus. In some embodiments, multiple steps or even all the steps may be carried out at least partly concurrently.

The method may further comprise causing printing of a protective layer on top of the components 12 to 18.

Figure 8:
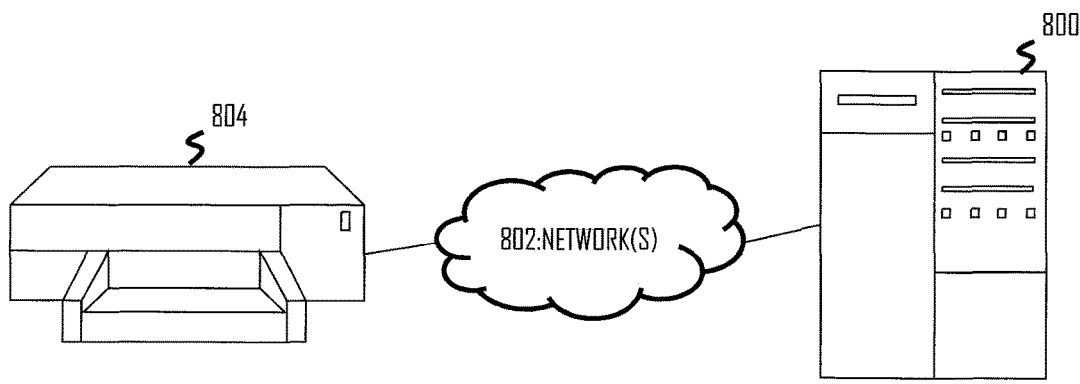
FIG. 8 illustrates a system for manufacturing of the apparatus according to an embodiment of the invention.

The method may be carried out by the printing apparatus in which case the printing apparatus may carry out the actual printing in steps 700 to 706. According to another aspect, the method may be carried out by the control apparatus in which case the control apparatus may provide the printing apparatus with instructions to carry out the printing of the apparatus. A communication connection may be provided between the control apparatus and the printing apparatus. The instructions provided by the control apparatus may specify a layout of the components on the base layer, the materials used for each component, etc. FIG. 8 illustrates an example of an environment in which the method may be carried out. The control apparatus may be a computer 800 such as a network server connected to a communication network 802, e.g. the Internet. The network server 800 may be accessed over one or more networks 802 and instructed to carry out the method of FIG. 7. The network server 800 may comprise at least one processor and at least one memory, wherein the memory may comprise a database storing definitions for printing the apparatus according to an embodiment of the invention. The memory may also store a computer program code causing the at least one processor to carry out the method of FIG. 7 and instruct the printing apparatus to print the apparatus on the base layer 10 according to the stored definitions of the apparatus. The network server 600 may be configured to access the printing apparatus 804 over the network(s) 802 and instruct the printing apparatus to carry out the printing of the components 12 to 18 on the base layer 10. The base layer 10 may be readily inserted into the printing apparatus by an operator. The printing apparatus may comprise a printing module, at least one processor, at least one memory, and a communication interface to communicate with the network server 800.

As described above, the apparatus comprising the base layer 10 and the components 12 to 18 may be an article of manufacture as a whole in which case the base layer 10 may also be a product. In other embodiments, the base layer 10 may be the user's skin or another layer that may not be manufactured.

The process or method described in FIG. 7 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

It should be appreciated that the present description provides only some embodiments of the invention, and further development may require extra changes to the described embodiments. Therefore, all words and expressions should be interpreted broadly and they are intended to illustrate, not to restrict, the embodiments. It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
   at least one base layer arranged as a substrate for printed electronics;
   an energy harvester printed on the at least one base layer and arranged to transform kinetic energy into electric energy;
   an energy storage printed on the at least one base layer, coupled to the energy harvester, and arranged to store the electric energy;
   a display element printed on the at least one base layer, coupled to the energy storage, and arranged to provide a display view to a user of the apparatus; and
   a control circuitry configured to determine the amount of the electric energy stored in the energy storage and to control the display element to update the display view according to the amount of the electric energy.

2. The apparatus of claim 1, wherein the energy harvester is the only energy source of the apparatus.

3. The apparatus of claim 1, wherein the electric energy transformed by the energy harvester is used as an energy source for providing said display element and the control circuitry with operating voltage and as a motion measurement signal measuring accumulated motion of the apparatus.

4. The apparatus of claim 3, wherein the apparatus is an activity monitoring apparatus, and wherein the control circuitry is configured to control the display element to output an indicator indicating the measured accumulated motion to a user of the apparatus.

5. The apparatus of claim 1, wherein the control circuitry comprises a comparator configured to compare the amount of electric energy stored in the energy storage with a determined threshold and, upon the amount of electric energy stored in the energy storage exceeds the determined threshold, to discharge at least some of the electric energy to the display element to change the contents of the display element.

6. The apparatus of claim 5, wherein the comparator comprises a Zener diode.

7. The apparatus of claim 1, wherein the control circuitry comprises at least one memristor, wherein the state of the memristor characterizes the amount of the electric energy.

8. The apparatus of claim 1, wherein the display element consumes energy only when updating the display view.

9. The apparatus of claim 8, wherein the display element comprises an electronic ink display.

10. The apparatus of claim 1, wherein the apparatus comprises a sticker.

11. The apparatus of claim 1, wherein the base layer is made of at least one of plastic and textile.

12. The apparatus of receding claim 1, wherein the apparatus is a disposable product.

13. A method for manufacturing an apparatus, comprising:
    causing printing of an energy harvester on at least one base layer serving as a substrate for printed electronics, wherein the energy harvester is arranged to transform kinetic energy into electric energy;
    causing printing of an energy storage on the at least one base layer and coupling of the energy storage to the energy harvester such that the energy storage stores the electric energy harvested by the energy harvester;
    causing printing of a display element on the at least one base layer and coupling of the display element to the energy storage, wherein the display element is arranged to provide a display view to a user of the apparatus; and
    causing printing of a control circuitry on the at least one base layer, wherein the control circuitry is printed such that it is capable of determining that a sufficient amount of energy is stored in the energy storage by the energy harvester and, as a consequence, control the display element to update the display view.

14. A computer program product embodied on a non-transitory distribution medium readable by a computer and comprising program instructions which, when executed by the computer, perform operations comprising:
    causing printing of an energy harvester on at least one base layer serving as a substrate for printed electronics, wherein the energy harvester is arranged to transform kinetic energy into electric energy;
    causing printing of an energy storage on the at least one base layer and coupling of the energy storage to the energy harvester such that the energy storage stores the electric energy harvested by the energy harvester;
    causing printing of a display element on the at least one base layer and coupling of the display element to the energy storage, wherein the display element is arranged to provide a display view to a user of the apparatus; and
    causing printing of a control circuitry on the at least one base layer, wherein the control circuitry is printed such that it is capable of determining that a sufficient amount of energy is stored in the energy storage by the energy harvester and, as a consequence, control the display element to update the display view.

* * * * *